United States Patent [19]

Poss

[11] Patent Number: 5,616,591

[45] Date of Patent: Apr. 1, 1997

[54] INDOLE- AND BENZIMIDAZOLE-SUBSTITUTED QUINOLINE DERIVATIVES

[75] Inventor: Michael A. Poss, Lawrenceville, N.J.

[73] Assignee: E.R. Squibb & Sons, Inc., Princeton, N.J.

[21] Appl. No.: 858,902

[22] Filed: Mar. 27, 1992

[51] Int. Cl.⁶ .............. A61K 31/47; C07D 215/233; C07D 401/12

[52] U.S. Cl. ............ 514/312; 514/314; 546/153; 548/311.1; 548/317.1; 548/492; 548/252

[58] Field of Search ............ 546/153; 548/337, 548/492, 311.1, 314.7; 514/312, 314

[56] References Cited

U.S. PATENT DOCUMENTS

| | | | |
|---|---|---|---|
| 3,184,462 | 5/1965 | Scarborough et al. | 546/153 X |
| 4,340,598 | 7/1982 | Furukawa et al. | 548/537 X |
| 4,355,040 | 10/1982 | Furukawa et al. | 548/337 X |
| 4,468,404 | 8/1984 | Rane et al. | 546/153 X |
| 4,582,847 | 4/1986 | Furukawa et al. | 548/337 X |
| 4,647,557 | 3/1987 | Moinet et al. | 546/153 X |
| 5,026,848 | 6/1991 | Daneshtalab et al. | 546/153 X |
| 5,068,337 | 11/1991 | Archibald et al. | 546/153 X |
| 5,071,860 | 12/1991 | Alig et al. | 546/153 X |

FOREIGN PATENT DOCUMENTS

| | | | |
|---|---|---|---|
| 323841 | 7/1989 | European Pat. Off. | 548/337 |
| 4128848 | 2/1990 | European Pat. Off. | 546/153 |
| 429257 | 5/1991 | European Pat. Off. | 548/337 |

*Primary Examiner*—Floyd D. Higel
*Attorney, Agent, or Firm*—Ellen K. Park

[57] ABSTRACT

Compounds of the formula

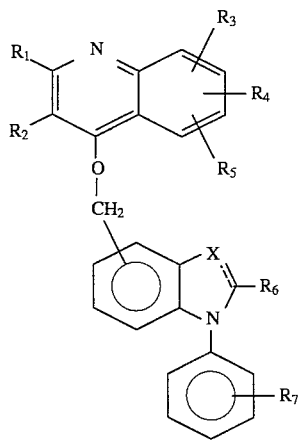

wherein X, $R_1$, $R_2$, $R_3$, $R_4$, $R_5$, $R_6$ and $R_7$ are as defined herein. These compounds inhibit the action of angiotensin II and are useful, therefore, for example, as antihypertensive agents.

9 Claims, No Drawings

INDOLE- AND BENZIMIDAZOLE-SUBSTITUTED QUINOLINE DERIVATIVES

FIELD OF THE INVENTION

The present invention relates to novel substituted quinolines which are useful as antihypertensive agents.

SUMMARY OF THE INVENTION

In accordance with the present invention, novel compounds which inhibit the action of the hormone angiotensin II are disclosed. These compounds are of the general formula

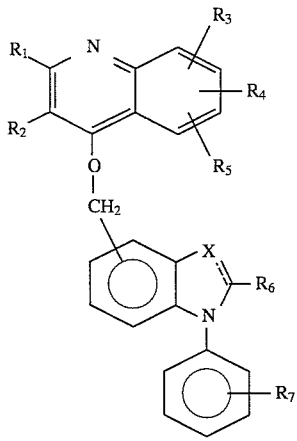

I and pharmaceutically acceptable salts and prodrugs thereof.

As used in formula I, and throughout the specification, the symbols have the following meanings:

X is

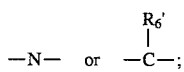

the broken line adjacent to the X atom represents the optional presence of a double bond, provided that if X is nitrogen, the double bond must be present;

$R_1$ is hydrogen, alkyl of 1 to 8 carbon atoms, alkoxy, cycloalkyl, (cycloalkyl)alkyl, haloalkyl, phenyl or arylalkyl;

$R_2$ is hydrogen, alkyl of 1 to 8 carbon atoms optionally substituted with one or more fluoro atoms, cycloalkyl, (cycloalkyl)alkyl, carboxy, alkoxycarbonyl, cyano, nitro, phenyl or arylalkyl;

$R_3$ is hydrogen, alkyl of 1 to 4 carbon atoms optionally substituted with one or more fluoro atoms, alkoxy of 1 to 4 carbon atoms, halogen, cyano or nitro;

$R_4$ and $R_5$ are independently selected from hydrogen; alkyl of 1 to 4 carbon atoms, optionally substituted with amino, halogen, hydroxy or alkoxy of 1 to 4 carbon atoms; alkoxy of 1 to 4 carbon atoms optionally substituted with halogen; halogen; hydroxy; cyano; nitro; amino; alkanoylamino of 1 to 4 carbon atoms; dialkylamino of up to 6 carbon atoms; (dialkylamino)alkyl of 3 to 8 carbon atoms; alkanoyl of 1 to 4 carbon atoms; carbamoyl; N-alkylcarbamoyl or di-(N-alkyl)carbamoyl of up to 7 carbon atoms; carboxy; alkoxycarbonyl of 1 to 4 carbon atoms; alkylthio of 1 to 6 carbon atoms; alkylsulphinyl of 1 to 6 carbon atoms; or alkylsulphonyl of 1 to 6 carbon atoms; or $R_4$ and $R_5$ together form an alkylenedioxy of 1 to 4 carbon atoms, when bonded to adjacent carbon atoms;

$R_6$ and $R_6'$ are independently selected from hydrogen, alkyl, aryl, cycloalkyl, arylalkyl, haloalkyl,

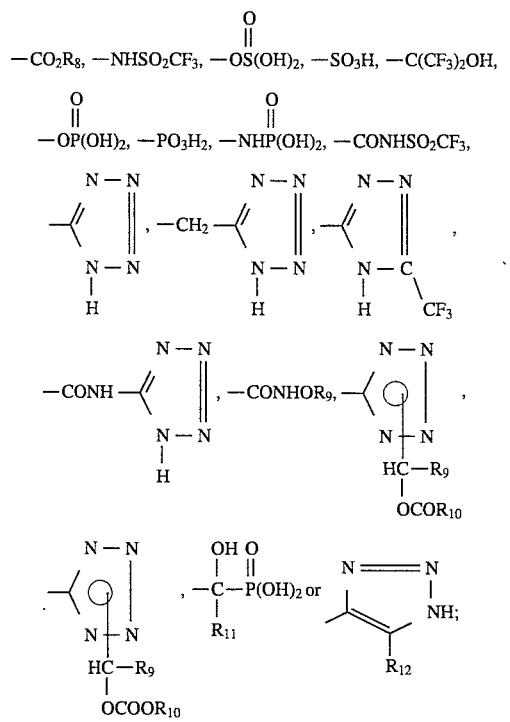

$R_7$ is an acid moiety such as hydrogen,

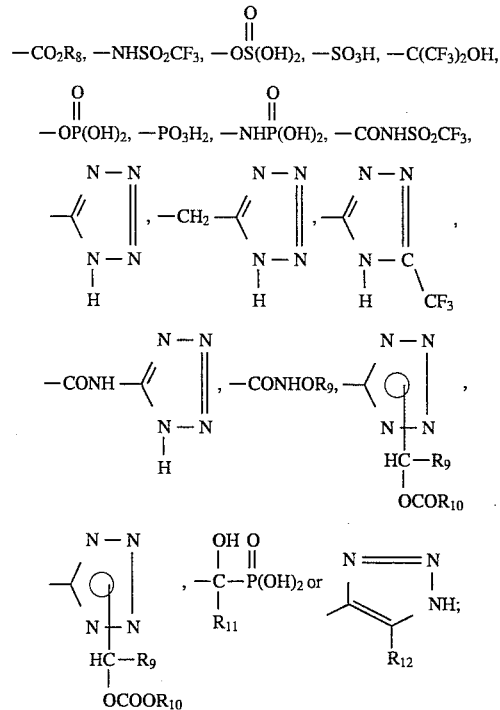

$R_8$ is hydrogen, alkyl, perfluoroalkyl of 1 to 8 carbon atoms, cycloalkyl of 3 to 6 carbon atoms, phenyl, benzyl,

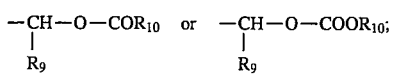

$R_9$ is hydrogen, alkyl, aryl, alkylaryl, arylalkyl or cycloalkyl;

$R_{10}$ is alkyl, aryl, alkylaryl, arylalkyl or cycloalkyl;

$R_{11}$ is hydrogen, alkyl of 1 to 5 carbon atoms or phenyl; and $R_{12}$ is —CN, —$NO_2$ or —$CO_2R_8$.

DETAILED DESCRIPTION OF THE INVENTION

The present invention relates to the compounds of formula I (and pharmaceutically acceptable salts and prodrugs thereof), to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

All stereoisomers of the compounds of the instant invention are contemplated, either in admixture or in pure or substantially pure form.

It should be understood that the present invention includes prodrug forms, such as ester, acetal and/or mixed acetal derivatives of the compounds of formula I. For example, such derivatives have been documented in *Design of Prodrugs*, edited by H. Bundgard, (Elsevier, 1985) and *Methods in Enzymology*, Vol. 42, p. 309–396, edited by K. Widder et al. (Academic Press, 1985). Further, it is understood that any moiety at $R_6$ and/or $R_7$ that will be cleaved in vivo to provide an acidic $R_6$ and/or $R_7$ moiety is within the spirit and scope of this invention.

An exemplary process for preparing the compounds of formula I includes coupling a compound of the formula

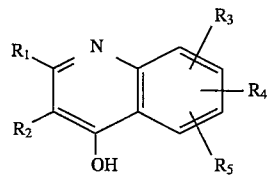

II with a compound of the formula

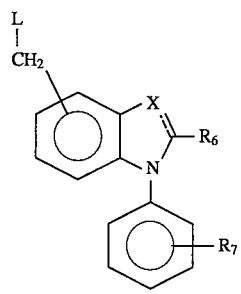

III wherein L is a leaving group such as a halogen, in the presence of a coupling agent such as cesium carbonate, in an organic solvent such as tetrahydrofuran or dimethylformamide.

The quinoline of formula II, where $R_1$ is methyl, and $R_2$, $R_3$, $R_4$ and $R_5$ are hydrogen, is commercially available. Other quinolines of formula II can be prepared according to procedures disclosed in EP 0 412 848 to Imperial Chemical Industries.

Compounds of formula III where X is

can be prepared by coupling a compound of the formula

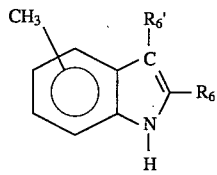

VI with a compound of the formula

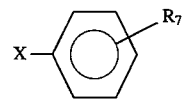

VII where X is bromide in a polar solvent such as pyridine in the presence of a catalyst such as copper oxide, to provide compounds of the formula

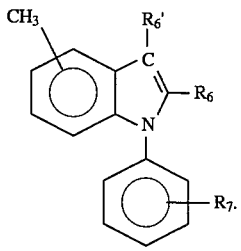

VIII

A leaving group, L, for example a halogen can be added by known methodology to provide compounds of the formula

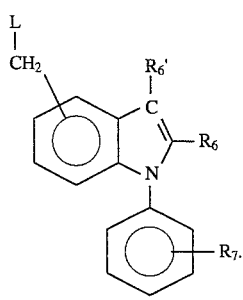

IIIa

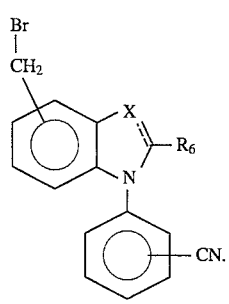

XII

Compounds of formula VI can be prepared by known techniques such as those described in *J. Heterocyclic Chem.*, 25, 1 (1988).

Compounds of formula III where X is

or X is nitrogen may also be prepared by reacting a compound of the formula

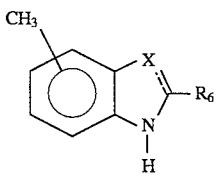

IX with a compound of the formula

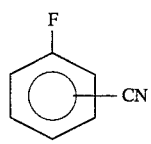

X in the presence of a base such as potassium carbonate in an organic solvent such as dimethylformamide, to provide a compound of the formula

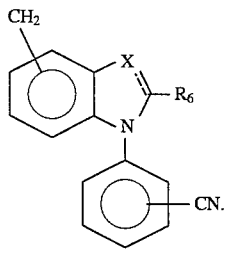

XI

Compound XI can thereafter be treated with a brominating agent such as N-bromosuccinimide and a radical initiator such as 2,2'-azobisisobuty-ronitrile, in an organic solvent such as carbon tetrachloride, to provide a compound of the formula Intermediate XII can be coupled with the quinoline of formula II to provide

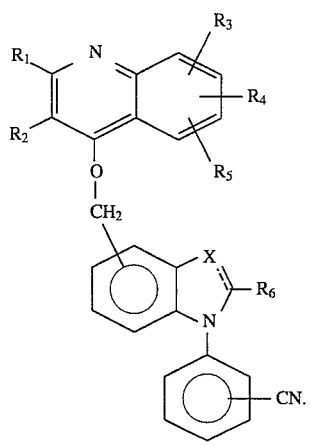

XIII

Compound XIII can then be reacted with an azide such as tributyltinazide to provide compounds of formula I where X is nitrogen and $R_7$ is

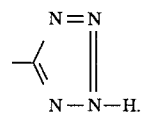

Compounds of formula I where X is nitrogen and $R_7$ is other than

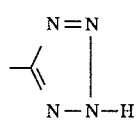

can be prepared by using intermediate VII (X=F) in place of compound X above.

Compounds of formula IX where X is nitrogen are prepared as described by Mathias et al., *Synthetic Communications*, 5, 461–469 (1975). Compounds of formulas VII and X are commercially available.

When preparing the compounds of the instant invention wherein the substituent groups contain one or more reactive functionalities such as hydroxy, amino, tetrazolyl, carboxyl, mercapto or imidazolyl groups, it may be necessary to protect these groups during the reactions in which they are used. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein $R_1$ is an alkyl of 1 to 8 carbons;
$R_2$ is hydrogen or an alkyl of 1 to 8 carbons;
$R_3$ is hydrogen;
$R_4$ is hydrogen or —$CO_2H$;
$R_5$ is hydrogen or —$CO_2H$;
$R_6$ is hydrogen or —$CO_2H$;
$R_7$ is ortho-tetrazolyl or —$CO_2H$; and
X is

where $R_6'$ is hydrogen or —$CO_2H$; or —N—.

Most preferred are compounds of formula I wherein
$R_1$ is methyl;
$R_2$ is hydrogen;
$R_3$ is hydrogen;
$R_4$ is hydrogen or —$CO_2H$;
$R_5$ is hydrogen or —$CO_2H$;
$R_6$ is hydrogen or —$CO_2H$
$R_7$ is ortho-tetrazolyl;
X is

where $R_6'$ is hydrogen; the double bond is present; and the quinoline nucleus is bonded to the 4-position of the indole.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the renin-angiotensin system described above., the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable,dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

2-Methyl-4-[[1-[2-(2H-tetrazol-5-yl)phenyl]-1H-indol-4-yl] methoxy]quinoline, trifluoroacetate (1:1) salt A. 1H-Indole-4-carboxylic acid, methyl ester To a solution of indole-4-carboxylic acid (506 mg, 3.14 mmol) dissolved in a mixture of methanol (5 mL) and diethyl ether (10 mL) was added ethereal diazomethane until disappearance of starting acid was indicated by TLC. Anhydrous magnesium sulfate was then added and the solution filtered and concentrated in vacuo. Flash chromatography on 10 g of Merck silica gel eluted with 2:1, chloroform:hexanes, followed by 10:1, chloroform:diethyl ether afforded the title compound (540 mg, 98%).

B. 1-(2-Cyanophenyl)-1H-indole-4-carboxylic acid, methyl ester

A mixture of the title A compound (40.6 mg, 0.232 mmol), 2-fluorobenzonitrile (38 μL, 0.348 mmol), potassium carbonate (64.1 mg, 0.464 mmol), and 18-crown-6 (6.1 mg, 0.0232 mmol) in 0.23 mL of dimethylformamide was heated at 150° C. for 150 minutes. Upon cooling to room temperature, the reaction mixture was diluted with ethyl acetate, filtered and rinsed with pH 4 buffer. The aqueous layer was further extracted with two more portions of ethyl acetate and the combined organic extract was rinsed with brine, dried over sodium sulfate, filtered through magnesium sulfate and concentrated in vacuo. Flash chromatography on 5 g of Merck silica gel eluted with 5:1, chloroform: hexanes, followed by 100% chloroform afforded the title compound (61.6 mg, 96%).

C. 1-[2-[2-(Triphenylmethyl)-2H-tetrazol-5-yl]phenyl]-1H-indole-4-carboxylic acid, methyl ester An initially heterogeneous mixture of the title B compound (8 g, 29 mmol), tri-n-butyltin azide (14.6 g, 44 mmol) and xylenes (20 mL) was heated at 130° C. overnight in a stoppered flask. The cooled reaction mixture was next concentrated in vacuo and treated with methanol (20 mL) and acetic acid (20 mL) for three hours, then concentrated again in vacuo and the acetic acid removed by evaporation with toluene. To the resulting crude reaction mixture was added triphenylmethyl chloride (10.5 g, 37.7 mmol), triethylamine (8.1 mL, 58.1 mmol) and acetone (110 mL) and the stoppered solution was stirred at room temperature for two days. After removing the acetone in vacuo, the product was partitioned between methylene chloride and half-saturated brine. The organic extract was rinsed with brine, dried (magnesium sulfate) and concentrated. Trituration with ethyl acetate/hexanes gave the title compound (15.79 g, 97%).

D. 1-[2-[2-(Triphenylmethyl)-2H-tetrazol-5-yl]phenyl]-1H-indole-4-methanol

The title C compound (15.7 g, 28 mmol) was dissolved in anhydrous tetrahydrofuran (140 mL), cooled to 0° C., and then treated with a 1M solution of lithium aluminum hydride in tetrahydrofuran (65 mL, 65 mmol). After three hours at 0° C., TLC of a reaction aliquot showed absence of starting material. The reaction was carefully quenched at 0° C. by addition sequentially of water (2.6 mL), 15% aqueous sodium hydroxide (2.6 mL) and water (7.9 mL). The resulting mixture was diluted with ethyl acetate, filtered through Celite, dried (magnesium sulfate) and concentrated. Trituration with ethyl acetate/hexanes yielded the title compound (13.35 g, 89%).

E. 4-(Bromomethyl)-1-[2-[2-(triphenylmethyl)-2H-tetrazol-5-yl]-phenyl]-1H-indole To a mixture of the title D compound (2.73 g, 5.12 mmol) and carbon tetrabromide (2.38 g, 7.16 mmol) in methylene chloride (20 mL) cooled to 0° C. was added triphenylphosphine (1.74 g, 6.65 mmol). After 30 minutes, the reaction was allowed to warm to room temperature and stirred for another four hours, then concentrated in vacuo and triturated with dichloromethane/hexanes to afford 2.46 g of crude material. Trituration again with dichloromethane/hexanes yielded 1.34 g of the title compound, and trituration of the accompanying mother liquor with acetone/hexanes gave another 1.05 g of product. Total yield of the title compound was 2.39 g (78%) of material with acceptable purity.

F. 2-Methyl-4-[[1-[2-[2-(triphenylmethyl)-2H-tetrazol-5-yl]phenyl]-1H-indole-4-yl]methoxy]quinoline To a sparged solution of 4-hydroxy-2-methyl quinoline (381 mg, 2.39 mmol) in dimethylformamide (5.2 mL) was added the title E compound (796 mg, 1.3 mmol) and cesium carbonate (1.5 g, 4.7 mmol). After stirring 20 hours at room temperature, the reaction was diluted with ethyl acetate and filtered. The organic solution was washed with pH 4 buffer (2×20 mL), saturated sodium bicarbonate (25 mL), water (3×25 mL), saturated sodium chloride (25 mL), dried over magnesium sulfate, filtered and concentrated to give an orange solid. Purification by Merck silica gel (80 g), eluting with 3:2 hexane/ethyl acetate gave (708 mg, 79%) of the title compound.

G. 2-Methyl-4-[[1-[2-(2H-tetrazol-5-yl)phenyl]-1H-indol-4-yl]methoxy]quinoline, trifluoro-acetate (1:1) salt To a solution of the title F compound (600 mg, 0.89 mmol), in dioxane (12 mL) was slowly added a saturated solution of hydrochloric acid/dioxane (4.2 mL). After 25 minutes at room temperature, the reaction was concentrated in vacuo and chased with ether. The gummy material was triturated with ether to yield a white solid. Purification by preparative HPLC (YMC S-10-ODS 30×500 mm, 65 mL/minute, λ=220 nm, eluting with an isocratic mixture of 58% of a solution of 90% methanol, 10% water, 0.5% trifluoroacetic acid and 42% of a solution of 10% methanol, 90% water, 0.5% trifluoroacetic acid) gave a yellow solid. The solid was triturated from methanol to give the title compound as a white solid (137 mg; 33%).

EXAMPLE 2

4-[[(2-Methyl-4-quinolinyl)oxy]methyl]-1-[2-(2H-tetrazol-5-yl)phenyl]-1H-indole-2-carboxylic acid, trifluoroacetate (1:1) salt A. 4-(Bromomethyl)-1-(2-cyanophenyl)-1H-indole-2-carboxylic acid, ethyl ester 1. 2-Methyl-6-nitro-α-oxobenzenepropanoic acid Sodium (3.802 g, 165.38 mmol, 2.5 eq) was added portionwise into ethanol (66 mL, 1M) at 0° C. Next, 3-nitro-ortho-xylene (10.00 g, 66.15 mmol, 1 eq) and diethyl oxalate (19.33 g, 132.23 mmol, 2 eq) were added. The mixture was stirred at room temperature for 18 hours and then refluxed for 10 minutes. 1N sodium hydroxide and water were added and the reaction was stirred for one hour. The ethanol was removed under vacuum. Water was added and the aqueous solution was acidified with concentrated hydrochloric acid to ph~2. The mixture was extracted with methylene chloride. The extracts were dried (magnesium sulfate) and concentrated to give the title compound (9.0 g, 61%).

2. 4-Methyl-1H-indole-2-carboxylic acid, ethyl ester

A mixture of the title 1 compound (8.560 g, 38.353 mmol), 10% palladium on charcoal (1.712 g, 20% by wt.) and methanol (76.7 mL, 0.5M) was shaken under hydrogen (50 PSI) for five hours. After filtration, the solvent was evaporated to give an intermediate.

A mixture of the intermediate, ethyliodide (17.945 g, 115.059 mmol, 3 eq), sodium bicarbonate (9.666 g, 115.059 mmol, 3 eq) and dimethylformamide (76.7 mL, 0.5M) was stirred at 50° C. for a total of 6.5 hours. At five hours, additional ethyliodide (5.982 g, 38.353 mmol, 1 eq) was added. After cooling, the reaction mixture was added into water (160 mL) and then the mixture was extracted with Hexane-ether (1:1) (5×160 mL). The extract was washed with sodium bicarbonate (150 mL, 10%), saturated sodium bicarbonate (150 mL) and saturated sodium chloride water solution (150 mL), dried (magnesium sulfate), filtered and concentrated. The residue was chromatographed on silica gel eluting with ethyl acetate in Hexane (1:20) to give the title compound (5.201 g, 66% for two steps).

3. 1-(2-Cyanophenyl)-4-methyl-1H-indole-2-carboxylic acid, ethyl ester

A mixture of the title 2 compound (2.710 g, 13.334 mmol, 1 eq), 2-fluorobenzonitrile (6.460 g, 50.336 mmol, 4 eq), potassium carbonate (3.686 g, 26.668 mmol, 2 eq), 18-Crown-6 (881 mg, 3.334 mmol, 0.25 eq) and dimethylformamide (13.33 mL, 1M) was stirred at 150° C. for a total of 31 hours. At 14 hours, more 2-fluorobenzonitrile (2.232 g, 18.429 mmol, 1.38 eq) was added and at 17 hours, additional 18-Crown-6 (400 mg, 0.113 eq) was added. The mixture was cooled and diluted with ethyl acetate. After filtration, the filtrate was washed with pH=4 buffer and saturated sodium chloride, dried (magnesium sulfate) and concentrated. The remaining material was chromatographed on silica gel eluting with Hexane:ether (8:1) to give the title compound (2.026 g, 50%).

4. 4-(Bromomethyl)-1-(2-cyanophenyl)-1H-indole-2-carboxylic acid, ethyl ester A mixture of the title 3 compound (2.096 g, 6.887 mmol, 1 eq), N-bromosuccinimide (1.287 g, 7.231 mmol, 1.05 eq), azobisisobutyronitrile (63 mg, 3% by wt) and carbon tetrachloride (115 mL, 0.06M) was refluxed for 2.5 hours. After cooling, dichloromethane was added into the reaction mixture. The organic liquid was washed with water, dried (magnesium sulfate) and concentrated. The residue was chromatographed on silica gel eluting with Hexane:dichloromethane (3:4) to give the title compound (2.550 g, 96%).

B. 1-(Cyanophenyl)-4-[[(2-methyl-4-quinolinyl)-oxy]methyl]-1H-indole-2-carboxylic acid, ethyl ester To a solution of 4-hydroxy-2-methyl quinoline (500 mg, 3.14 mmol) in dimethylformamide (7.2 mL) sparged with argon 15 minutes, was added the title A compound (800 mg, 2.09 mmol) and crushed cesium carbonate (2.04 g, 6.27 mmol). After 24 hours, the reaction was concentrated in vacuo. The residue was washed with pH=4 buffer (2×), pH=7 buffer (3×), and saturated sodium chloride, dried over magnesium sulfate, filtered and concentrated to a brown foam. Trituration with 1:1 ether:hexane followed by 1:1 ethyl acetate: hexane gave 633 mg (62%) of the product as a white solid. The filtrate was concentrated and purified by flash chromatography (31 g Merck silica gel; 60% ethyl acetate/hexane) to give the desired product (72.5 mg), and a total yield of 705 mg, (69%).

C. 4-[[2-Methyl-4-quinolinyl)oxy]methyl]-1-2-(2H-tetrazol-5-yl)phenyl]-1H-indole-2-carboxylic acid, ethyl ester A solution of tributyltinazide (574 mg, 1.73 mmol) and the title B compound (200 mg, 0.43 mmol) in xylenes (2.23 mL) was heated at 100° C. for 24 hours. Purification by flash chromatography (22 g Merck silica gel; (95:5:0.5) dichloromethane: methanol: Acetic Acid) gave the desired product (194 mg, 89%).

D. 4-[[(2-Methyl-4-quinolinyl)oxy]methyl]-1-[2-(2H-tetrazol-5-yl)phenyl]-1H-indole-2-carboxylic acid, trifluoroacetate (1:1) salt To the title C compound (180 mg, 0.36 mmol) in ethanol (1.8 mL) was added 1N lithium hydroxide (1.79 mL, 1.79 mmol). After stirring 24 hours at room temperature, the reaction was concentrated in vacuo, dissolved in water and acidified to pH=2.5, but the solid obtained was not filterable. Purification by preparative HPLC (YMC S-10-ODS 30×500 mm, 26 mL/minute flow rate, λ=220 nm, 55% isocratic solution of 90% methanol, 10% water, 0.5% trifloroacetic acid (solvent B); 10% methanol, 90% water, 0.5% trifloroacetic acid (solvent A)), gave the title compound as a white solid (260.3 mg; 53%).

What is claimed is:

1. A compound of the formula

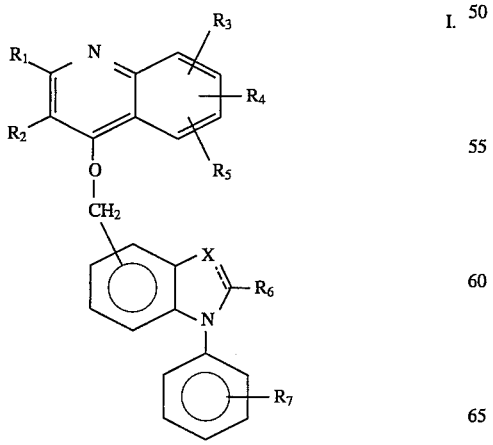

or a pharmaceutically acceptable salt or prodrug thereof;

wherein X is —N— or

the broken line adjacent to the X atom represents the possible presence of a double bond, provided that if X is nitrogen, the double bond must be present;

$R_1$ is hydrogen, alkyl of 1 to 8 carbon atoms, alkoxy, cycloalkyl, (cycloalkyl)alkyl, haloalkyl, phenyl or arylalkyl;

$R_2$ is hydrogen, alkyl of 1 to 8 carbon atoms unsubstituted or substituted with one or more fluoro atoms, cycloalkyl, (cycloalkyl)alkyl, carboxy, alkoxycarbonyl, cyano, nitro, phenyl or arylalkyl;

$R_3$ is hydrogen, alkyl of 1 to 4 carbon atoms unsubstituted or substituted with one or more fluoro atoms, alkoxy of 1 to 4 carbon atoms, halogen, cyano or nitro;

$R_4$ and $R_5$ are independently selected from hydrogen; alkyl of 1 to 4 carbon atoms, unsubstituted or substituted with amino, hydroxy or alkoxy of 1 to 4 carbon atoms; alkoxy of 1 to 4 carbon atoms unsubstituted or substituted with halogen; halogen; hydroxy; haloalkyl; cyano, nitro; amino; alkanoylamino of 1 to 4 carbon atoms; alkylamino or dialkylamino of up to 6 carbon atoms; (dialkylamino)alkyl of 3 to 8 carbon atoms; alkanoyl of 1 to 4 carbon atoms; carbamoyl; N-alkylcarbamoyl or di-(N-alkyl)carbamoyl of up to 7 carbon atoms; carboxy; alkoxycarbonyl of 1 to 4 carbon atoms; alkylthio of 1 to 6 carbon atoms; alkylsulphinyl of 1 to 6 carbon atoms; or alkylsulphonyl of 1 to 6 carbon atoms; or $R_4$ and $R_5$ together form an alkylenedioxy of 1 to 4 carbon atoms, when bonded to adjacent carbon atoms;

$R_6$ and $R_6{'}$ are independently selected from hydrogen, alkyl, aryl, cycloalkyl, arylalkyl, haloalkyl,

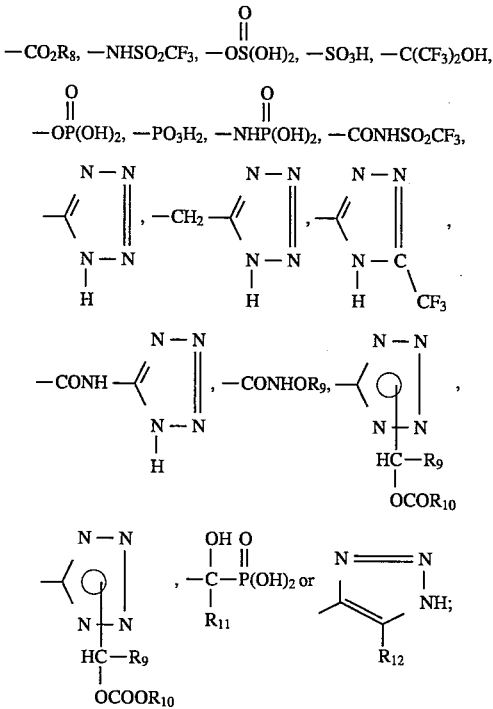

13
-continued $R_7$ is hydrogen, $-CO_2R_8$, $-NHSO_2CF_3$, $-OS(OH)_2$,
$-SO_3H$, $-C(CF_3)_2OH$, $-OP(OH)_2$, $-PO_3H_2$, $-NHP(OH)_2$,
$-CONHSO_2CF_3$,

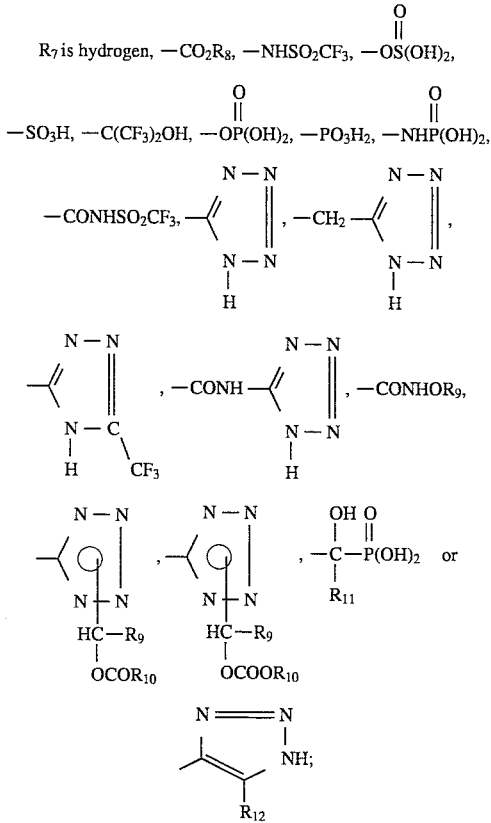

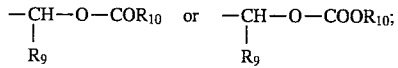

$R_8$ is hydrogen, alkyl, perfluoroalkyl of 1 to 8 carbon atoms, cycloalkyl of 3 to 6 carbon atoms, phenyl, benzyl, $$-\underset{\underset{R_9}{|}}{CH}-O-COR_{10} \text{ or } -\underset{\underset{R_9}{|}}{CH}-O-COOR_{10};$$

$R_9$ is hydrogen, alkyl, aryl, alkylaryl, arylalkyl, or cycloalkyl;

$R_{10}$ is alkyl, aryl, alkylaryl, arylalkyl or cycloalkyl;

$R_{11}$ is hydrogen, alkyl of 1 to 5 carbon atoms or phenyl; and $R_{12}$ —CN, $-NO_2$ or $-CO_2R_8$.

2. A compound of claim 1 wherein
$R_1$ is an alkyl of 1 to 8 carbons;
$R_2$ is hydrogen or an alkyl of 1 to 8 carbons;

14

$R_3$ is hydrogen;
$R_4$ is hydrogen or $-CO_2H$;
$R_5$ is hydrogen or $-CO_2H$;
$R_6$ is hydrogen or $-CO_2H$;
$R_7$ is ortho-tetrazolyl or $-CO_2H$; and
X is

where $R_6'$ is hydrogen or $-CO_2H$; or $-N-$.

3. A compound of claim 1 wherein
$R_1$ is methyl;
$R_2$ is hydrogen;
$R_3$ is hydrogen;
$R_4$ is hydrogen or $-CO_2H$;
$R_5$ is hydrogen or $-CO_2H$;
$R_6$ is hydrogen or $-CO_2H$
$R_7$ is ortho-tetrazolyl;
X is

where $R_6'$ is hydrogen; the double bond is present; and the quinoline portion is bonded to the 4-position of the indole.

4. A compound of claim 1, 2-Methyl-4-[[1-[2-(2H-tetrazol-5-yl)phenyl]-1H-indol-4-yl]methoxy]-quinoline, or a pharmaceutically acceptable salt or prodrug thereof.

5. A compound of claim 1, 4-[[(2-Methyl-4-quinolinyl)oxy]methyl]-1-[2-(2H-tetrazol-5-yl)phenyl]-1H-indole-2-carboxylic acid or a pharmaceutically acceptable salt or prodrug thereof.

6. A pharmaceutical composition comprising a compound of claim 1 and a pharmaceutically acceptable carrier.

7. A method for treating hypertension comprising administering to a mammalian specie in need thereof a therapeutically effective amount of a composition of claim 6.

8. A method for treating congestive heart failure comprising administering to a mammalian specie in need thereof a therapeutically effective amount of a composition of claim 6.

9. A method for treating cardiac hypertrophy comprising administering to a mammalian specie in need thereof a therapeutically effective amount of a composition of claim 6.

* * * * *